US011041142B2

(12) United States Patent
Anker et al.

(10) Patent No.: US 11,041,142 B2
(45) Date of Patent: Jun. 22, 2021

(54) METHOD AND DEVICE SUITABLE FOR GROWING ALGAE

(71) Applicant: ARIEL SCIENTIFIC INNOVATIONS LTD, Ariel (IL)

(72) Inventors: Yaakov Anker, Salit (IL); Erez Katz, Salit (IL); David Mualem, Kfar Saba (IL)

(73) Assignee: ARIEL SCIENTIFIC INNOVATIONS LTD., Ariel (IL)

( * ) Notice: Subject to any disclaimer, the term of this patent is extended or adjusted under 35 U.S.C. 154(b) by 88 days.

(21) Appl. No.: 15/796,877

(22) Filed: Oct. 30, 2017

(65) Prior Publication Data

US 2018/0072983 A1 Mar. 15, 2018

Related U.S. Application Data

(63) Continuation of application No. 14/438,657, filed as application No. PCT/IB2013/060004 on Nov. 8, 2013, now abandoned.

(60) Provisional application No. 61/723,799, filed on Nov. 8, 2012.

(51) Int. Cl.
*C12N 1/12* (2006.01)
*C12M 1/00* (2006.01)
*C12M 1/26* (2006.01)

(52) U.S. Cl.
CPC .............. *C12N 1/12* (2013.01); *C12M 21/02* (2013.01); *C12M 29/00* (2013.01); *C12M 33/00* (2013.01); *C12M 33/20* (2013.01)

(58) Field of Classification Search
CPC .................................................... C12M 21/02

USPC ........................................................ 435/292.1
See application file for complete search history.

(56) References Cited

U.S. PATENT DOCUMENTS

| 4,209,943 | A | * | 7/1980 | Moeller | A01G 9/18 47/1.4 |
|---|---|---|---|---|---|
| 2008/0155890 | A1 | * | 7/2008 | Oyler | A01G 22/00 47/1.4 |
| 2008/0274494 | A1 | * | 11/2008 | Kertz | A01G 7/02 435/29 |
| 2009/0126265 | A1 | * | 5/2009 | Rasmussen | A01G 33/00 47/1.4 |
| 2010/0216218 | A1 | * | 8/2010 | Huang | C12M 21/02 435/257.3 |
| 2012/0107919 | A1 | * | 5/2012 | Broneske | C12M 25/01 435/257.1 |
| 2012/0252105 | A1 | * | 10/2012 | Ahrens | C12M 21/02 435/257.3 |
| 2012/0294788 | A1 | * | 11/2012 | Walsh, Jr. | A01G 9/243 423/225 |

(Continued)

FOREIGN PATENT DOCUMENTS

CN 202246641 U * 5/2012 ............ C12M 21/02
JP 61249382 A * 11/1986

OTHER PUBLICATIONS

Machine translation of JP-61249382-A provided by Espacenet entitled JPS61249382A Spray Culture Device for Diatom (Year: 1986).*

(Continued)

*Primary Examiner* — Holly Kipouros
(74) *Attorney, Agent, or Firm* — Howard & Howard Attorneys PLLC (57) ABSTRACT

Disclosed are methods and devices suitable for growing algae.

18 Claims, 6 Drawing Sheets

(56) References Cited

U.S. PATENT DOCUMENTS

2013/0102056 A1* 4/2013 Suryo .................... C12M 21/02
435/252.1

OTHER PUBLICATIONS

Machine translation of CN 202246641 provided by Espacenet entitled Description CN202246641U Photobioreactor for runway pond (Year: 2012).*

* cited by examiner

METHOD AND DEVICE SUITABLE FOR GROWING ALGAE

RELATED APPLICATIONS

The present application gains priority from U.S. Provisional Patent Application 61/723,799 filed 8 Nov. 2012 which is incorporated by reference as if fully set-forth herein. The present application is related to PCT Patent Application IB2012/000884 filed 6 May 2012 and published on 15 Nov. 2012 as WO2012/153174 which is incorporated by reference as if fully set-forth herein.

FIELD AND BACKGROUND OF THE INVENTION

The invention, in some embodiments, relates to the field of algaculture, and more particularly, but not exclusively, to methods and devices suitable for growing algae, especially microalgae.

Commercial algaculture is important for producing products for many industries including food, cosmetics, pharmaceutical, chemical and fuel industries.

Methods and devices for growing algae are sought after.

SUMMARY OF THE INVENTION

Some embodiments of the invention herein provide methods and devices for growing algae, especially microalgae, that are in some aspects advantageous over those known in the art.

According to an aspect of some embodiments of the invention, there is provided a method for growing algae, comprising: providing algae growth liquid at a first position; and allowing the algae growth liquid to move from the first position to a reservoir while passing through a gaseous atmosphere; wherein the reservoir is lower than the first position. In some embodiments, the method further comprises, during the passing of the algae growth liquid through the atmosphere to the reservoir, the algae growth liquid serially contacting a number of intermediate stages that delay movement of the algae growth liquid to the reservoir, wherein the number of intermediate stages is at least one.

According to an aspect of some embodiments of the invention, there is also provided a device for growing algae comprising:
  a. a reservoir suitable for holding algae growth liquid; and
  b. a liquid transport assembly defining a conduit for algae growth liquid from the reservoir to a first position of the liquid transport assembly, the first position higher than the reservoir,
wherein the first position includes at least one aperture, the at least one aperture configured to allow algae growth liquid removed from the reservoir to move back to the reservoir while passing through a gaseous atmosphere.

In some embodiments, the device further comprises a number of intermediate stages, located at different heights, positioned so that algae growth liquid moving from the first position to the reservoir serially contacts the number of intermediate stages, thereby delaying the moving of algae growth liquid from the first position to the reservoir, wherein the number of intermediate stages is at least one. In some embodiments, the intermediate stages are located at different heights one from the other, the heights lower than the first position and higher than the reservoir.

Aspects of some embodiments of the teachings herein are complementary to or are partially dependent on the teachings of PCT Patent Application IB2012/000884 filed 6 May 2012 and published on 15 Nov. 2012 as WO2012/153174. Prior to publication, IB2012/000884 in its entirety was included as an Appendix in U.S. 61/723,799, the priority document of the instant application, inter alia, providing enabling support for aspects of the invention. Since WO2012/153174 has now been published, it is hereby included by reference as if fully set-forth herein.

Unless otherwise defined, all technical and scientific terms used herein have the same meaning as commonly understood by one of ordinary skill in the art to which the invention pertains. In case of conflict, the specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +/−10%.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

The invention, in some embodiments thereof, relates to methods and devices suitable for growing algae, especially microalgae, in some embodiments photoautotrophic algae and in some embodiments mixotrophic algae.

In some embodiments, algae grown according to the teachings herein are exposed to light to consume carbon dioxide and nutrients to produce algal biomass, in preferred embodiments under conditions that encourage photosynthesis at the expense of other forms of metabolism and/or that encourage algal lipid production and/or discourage lignin production.

In some embodiments, a device as described herein can be considered a photobioreactor. In some embodiments, a device as described herein can be considered a greenhouse suitable for growing algae.

In some embodiments, the teachings herein are useful for carbon-sequestering devices, for example, a device according to the teachings herein is associated with the exhaust of a carbon dioxide emitter (such as a fossil-fuel burning power plant) and at least some of the carbon dioxide in the exhaust is converted to algal biomass instead of being released into the atmosphere.

In some embodiments, the teachings herein are useful for wastewater processing, converting wastewater into algal biomass and clean water, in some embodiments similarly or substantially identically to that described in PCT Patent Application IB2012/000884.

In some embodiments, the teachings herein are useful for biofuel generation, converting sunlight into lipids, in some embodiments similarly or substantially identically to that described in PCT Patent Application IB2012/000884.

The principles, uses and implementations of the teachings of the invention may be better understood with reference to the accompanying description and figures. Upon perusal of the description and figures present herein, one skilled in the art is able to implement the teachings of the invention without undue effort or experimentation. In the figures, like reference numerals refer to like parts throughout.

Before explaining at least one embodiment of the invention in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

As detailed in PCT Patent Application IB2012/000884, it has been found that the mode of algae growth in an algae growth liquid can be modified by the conditions under which the algae are raised. By growing algae according to a suitable method and/or in a suitable device, algae can be grown with one or more of a relatively high yield, relatively high growth rate, relatively high lipid content, relatively low cellulose content and relatively low lignin content. Embodiments of the teachings herein implement at least some of these findings to provide methods and devices suitable for growing algae that have one or more advantages, in some embodiments including being simple and cheap to transport, establish, operate and maintain, even in remote and difficult to access locations.

Method for Growing Algae

According to an aspect of some embodiments of the teachings herein, there is provided a method for growing algae, comprising:

providing algae growth liquid at a first position; and allowing the algae growth liquid to move from the first position to a reservoir while passing through a gaseous atmosphere, wherein the reservoir is lower than the first position.

The algae growth liquid is any suitable algae growth liquid, typically water including algae or algae spores and nutrients required for and/or suitable for algae growth. Depending on the embodiment, the algae growth liquid is fresh, brackish or salt water.

The gaseous atmosphere is any suitable gaseous atmosphere and is typically air with optional minor changes in gas concentrations, for example, carbon dioxide enriched air.

In some embodiments, gas exchange is promoted as the algae growth liquid moves from the first position to the reservoir while passing through the gaseous atmosphere. Such gas exchange rids the algae growth liquid of excess molecular oxygen (a byproduct of photosynthesis) and allows the absorption of carbon dioxide from the atmosphere to support further photosynthesis. In some embodiments, such passing through the gaseous atmosphere helps avoid inducing at least some algae from adopting non-photosynthetic (respiratory) metabolism.

It has been found that for the purpose of absorbing carbon dioxide, in some embodiments, passing of the algae growth liquid through a gaseous atmosphere is superior to direct introduction (e.g., bubbling) of carbon dioxide gas into the algae growth liquid, by avoiding e*xcess carbon dioxide absorption that may arrest algae growth. Further, some embodiments are cheaper and easier to establish and maintain than direct introduction, typically not needing the active components such as pumps to implement direct introduction of gas into the algae growth liquid.

In some embodiments, exposure to sunlight for photosynthesis is increased as the algae growth liquid moves from the first position to the reservoir due to the greater surface area exposed to sunlight, the shorter optical path through the algae growth liquid and due to mixing of the algae growth liquid.

As discussed in detail in PCT Patent Application IB2012/000884, it has been found that algae that over time are allowed periods of rest (where the algae growth liquid does not move, or moves only slowly) alternating with periods of vigorous motion (where the algae growth liquid moves more vigorously, e.g., fast flow and/or mixing of the algae growth liquid) in some embodiments on the one hand helps prevent the algae from adopting a sessile growth mode and/or reduces the incidence of colony formation, and on the other hand helps prevent or reduce the incidence of algae developing swimming organs. In some embodiments, such conditions lead to algae having a high lipid content and relatively low cellulose and lignin content.

In some embodiments, the reservoir is located directly below the first position. In some embodiments, such a configuration allows the method to be implemented with a relatively small "footprint", that is to say, in a relatively small area.

In some embodiments, allowing the algae growth liquid to pass through the gaseous atmosphere to the reservoir is by dropping the algae growth liquid from the first position towards the reservoir, so the algae growth liquid falls into the reservoir by gravity. Such dropping is energy efficient as no external energy is expended to actively drive the algae growth liquid through the gaseous atmosphere. In some instances, such an embodiment is advantageously implemented when the reservoir is located directly below the first position.

In some embodiments, providing the algae growth liquid at the first position comprises transporting the algae growth liquid from the reservoir to the first position. In some embodiments, the algae growth liquid is transported from the reservoir to the first position by pumping. Any suitable pump can be used for transporting the algae growth liquid to the first position, for example, a circulation pump, an Archimedes' screw or a screw conveyer.

As noted above, as the algae growth liquid passes through a gaseous atmosphere while moving from the first position to the reservoir, gas exchange is effected with the gaseous atmosphere. The efficiency of such gas exchange is at least partially dependent on the surface area of the algae growth liquid, where greater surface area typically leads to more efficient gas exchange.

Accordingly, to promote efficient gas exchange, in some embodiments during at least part of the movement of the algae growth liquid from the first position to the reservoir, the algae growth liquid is in contact exclusively with the gaseous atmosphere, that is to say, substantially devoid (in preferred embodiments entirely devoid of) of contact with a physical component. As a result, a greater surface area of the moving algae growth liquid is in contact with the atmosphere and the atmosphere can more efficiently flow around the algae growth liquid. An embodiment of movement of algae growth liquid devoid of contact with a physical component is exemplified hereinbelow.

Further, to promote efficient gas exchange, in some embodiments the algae growth liquid passes through the gaseous atmosphere having a high surface area form. In some embodiments, such a high surface area form is selected from the group consisting of a plurality of droplets, a plurality of individual streams, at least one sheet of algae growth liquid and a spray, as opposed to, for example a single large-diameter laminar flow stream.

High surface area forms can be implemented using any suitable method, component or mechanism.

In some embodiments, the first position includes apertures (e.g., apertures in an algae growth liquid conduit) and the algae growth liquid moves from the first position through at least one aperture in the first position, e.g., a plurality of holes to make a plurality of individual streams, at least one gap or slit, for example between slats/bars to make at least one sheet. Typically, such apertures are relatively large, in some embodiments the apertures being at least 16 square millimeter in area.

In some embodiments, the algae growth liquid moves from the first position over a rim of the conduit, typically resulting in a plurality of individual streams (if the rim has crenelated or similar features) or a sheet (if the rim is smooth). For example, in some such embodiments the first position comprises an open algae growth liquid conduit (e.g., an open-topped conduit like a gutter or trough) and the algae growth liquid runs over the rim of the conduit.

In some embodiments, the algae growth liquid moves from the first position as a fountain or spray. In some instances, such embodiments typically require the expenditure of external energy to form the fountain or spray and may therefore be considered less advantageous for some implementations, for example compared to embodiments where the algae growth liquid is allowed to passively drop towards the reservoir. Additionally, implementation of a fountain or spray may require a component having small holes that are susceptible to blockage by the algae and are therefore disadvantageous.

In some embodiments, the algae growth liquid cascades while moving from the first position to the reservoir while passing through a gaseous atmosphere, that is to say, in some embodiments during the passing of the algae growth liquid through the atmosphere to the reservoir, the algae growth liquid serially contacts a number of intermediate stages that delay movement of the algae growth liquid to the reservoir, wherein the number of intermediate stages is at least one so that the algae growth liquid cascades to the reservoir. In some embodiments the number of intermediate stages is at least two. In some embodiments the number of intermediate stages is at least three. In some embodiments the number of intermediate stages is at least four. In some embodiments the number of intermediate stages is at least five.

Compared to direct movement of the algae growth liquid from the first position to the reservoir, cascading movement past a number of intermediate stages has been found to provide superior results. Although not wishing to be held to any one theory, it is believed that such superior results are a consequence of one or more of: additional rest/motion cycles (during contact with an intermediate stage/moving from an intermediate stage); superior mixing, and greater efficiency of gas exchange.

In some embodiments, the reservoir is located below the intermediate stage or stages, in some embodiments directly below the intermediate stage or stages. In some embodiments, such configuration allows the method to be implemented with a relatively small "footprint", that is to say, in a relatively small area. As noted above, in some embodiments, allowing the algae growth liquid to pass through the gaseous atmosphere to the reservoir is by dropping the algae growth liquid from the intermediate stage or stages. In some instances, such an embodiment is advantageously implemented when the reservoir is located below the intermediate stage or stages, in some embodiments directly below.

In some embodiments, the algae growth liquid contacts a surface of at least one intermediate stage.

In some embodiments, subsequent to contact with an intermediate stage, the algae growth liquid runs off a rim of the intermediate stage to continue moving to the reservoir (if relevant, first contacting at least one more intermediate stage). For example, in some such embodiments an intermediate stage is a plate, the algae growth liquid drops onto the surface of the plate and then runs off the rim of the plate.

Additionally or alternately, in some embodiments, subsequent to contact with a intermediate stage, the algae growth liquid passes through apertures (such as holes, gaps and slits) in the intermediate stage to continue moving to the reservoir (if relevant, first contacting at least one more intermediate stage). In some such embodiments, an intermediate stage is selected from the group consisting of nets, meshes, webs, apertured components such as plates or bowls, slats and bars. An advantage of some such embodiments is that the intermediate stage can be optionally configured to be concave so that the algae growth liquid is accumulated and therefore delayed for a substantial time in the concavity of the intermediate stage, but eventually passes through the apertures.

As described in PCT Patent Application IB2012/000884, extended periods of time without motion may induce algae to adopt a sessile form and/or to form colonies. To assist in preventing or reducing the incidence of the sessile form or colony formation, in some embodiments, the providing of the algae growth liquid at the first position (e.g., transporting from the reservoir) and the passing of the algae growth liquid through the atmosphere is for not less than 18 hours a day, in some embodiments for not less than 20 hours a day, for not less than 22 hours a day, and in some embodiments for substantially 24 hours a day. In some embodiments, the providing of the algae growth liquid at the first position and the passing through the atmosphere is substantially continuous. In some embodiments, the providing of the algae growth liquid at the first position and the passing through the atmosphere is intermittent. In some embodiments, the providing of the algae growth liquid through the atmosphere and the passing through the atmosphere is periodic.

Clearly, algae require sunlight for substantial photosynthesis. Accordingly, in some embodiments during at least a portion of the day, the algae growth liquid passing through the atmosphere is exposed to sunlight. In some embodiments, during at least a portion of the day, the algae growth liquid in the reservoir is exposed to sunlight.

As described in PCT Patent Application IB2012/000884, extended periods of time without light may induce some algae to adopt non-photosynthetic (respiratory) metabolism. Accordingly, to avoid or reduce the chance that some algae adopt non-photosynthetic metabolism, in some embodiments the method includes ensuring substantially continuous illumination of at least a portion of the algae growth liquid for not less than 16 hours a day, in some embodiments for not less than 18 hours a day, not less than 20 hours a day, not less than 22 hours a day and in some embodiments, even substantially 24 hours a day. In some embodiments, the method comprises:

during at least part of a day allowing a portion of the algae growth liquid to be illuminated by sunlight; or in the absence of sunlight, illuminating at least a portion of the algae growth liquid with artificial light.

As noted above, a suitable extent of gas exchange between the algae growth liquid and the atmosphere is typically advantageous for algae growth. In some embodiments, turbulence in the atmosphere caused by the movement of the algae growth liquid to the reservoir is sufficient for bringing fresh atmosphere in contact with the algae growth liquid. That said, in some embodiments, the method comprises actively generating gas flow in the atmosphere, for example, with the use of a blower or fan.

Carbon dioxide is consumed during photosynthesis. In some embodiments, the rate of photosynthesis and thus algae growth is increased by ensuring that a greater amount of carbon dioxide is present in the algae growth liquid to be available for the algae. That said, it has been found that an excessive amount of carbon dioxide in the algae growth liquid (for instance caused by excessively vigorous direct addition of carbon dioxide, for example by bubbling) can reduce the rate of algae growth. It has been found that in some embodiments additional carbon dioxide can be advantageously added to the algae growth liquid through the gas exchange mechanism described above by providing an atmosphere enriched in carbon dioxide or by enriching the atmosphere with carbon dioxide. Thus, in some embodiments, the atmosphere has a carbon dioxide content higher than that of ambient air (0.04%). In some embodiments, the method further comprises adding carbon dioxide to the atmosphere, so that the atmosphere has a carbon dioxide content higher than that of ambient air (0.04%).

In some embodiments, the first position of the liquid transport assembly is contained in an internal volume of an enclosure so that the enclosure constitutes a greenhouse. In some embodiments, the liquid transport assembly is also contained in the internal volume of the enclosure. In some embodiments, at least part of, and in some embodiments substantially all of, the reservoir is also contained in the internal volume of the enclosure. In some embodiments, intermediate stages are contained in the internal volume of the enclosure. In some embodiments, a sufficient portion of the enclosure is substantially transparent so as not to substantially interfere with passage of sunlight necessary for photosynthesis. Depending on the embodiment and substantially in the manner of a prior art greenhouse, such an enclosure may provide one or more advantages, for example: helps maintain the required temperature of the algae growth liquid, reduces undesirable effects of water evaporation, assists in preventing contamination of the algae growth liquid (e.g., with unwanted bacteria or algae that potentially compete for resources with the desired algae), and/or assists in maintaining a higher than ambient carbon dioxide content of the atmosphere. The enclosure may be fashioned of any suitable material including glass and suitable transparent polymers (e.g., polycarbonate, PMMA). That said, in some embodiments a preferred material is transparent polyethylene film, preferably flexible, as known in the field of agriculture, as these are cheap, readily available and easy to work. In some embodiments, the atmosphere in the internal volume of such an enclosure is maintained at a higher than ambient air pressure, as described in greater detail hereinbelow.

As noted above, any suitable algae growth liquid may be used. As described in PCT Patent Application IB2012/000884, in some embodiments it is advantageous to prevent other organisms from competing with the algae for resources in the algae growth liquid. Accordingly, in some embodiments the algae growth liquid is substantially devoid of a viable aerobic bacteria population. In some embodiments, the algae growth liquid is substantially devoid of a viable facultative bacteria population.

In some embodiments, the method further comprises adding an aqueous influent to the reservoir. In some embodiments, influent is added directly to the reservoir. Alternatively or additionally, in some embodiments, influent is added to the first position. Alternatively or additionally, in some embodiments, influent is added at an intermediate stage. In some embodiments, adding aqueous influent is substantially continuous. In some embodiments, adding aqueous influent is periodic. In some embodiments, adding aqueous influent is intermittent.

Any suitable aqueous influent may be added. Depending on the embodiment, the influent is fresh, brackish or salt water. In some embodiments, the influent includes fertilizer. In some embodiments, the influent is wastewater (e.g., as described in PCT Patent Application IB2012/000884). In some embodiments, the influent is processed wastewater and the implementation of the method is for polishing of the processed wastewater. As noted above, in some embodiments it is preferred that no other organisms be present in the algae growth liquid to compete with the algae for resources. Accordingly, in some embodiments the aqueous influent is substantially devoid of a viable aerobic bacterial population and in some embodiments the aqueous influent is substantially devoid of a viable facultative bacterial population. As described in PCT Patent Application IB2012/000884, one suitable method for reducing or eliminating viable populations of aerobic and/or facultative bacteria from aqueous influent such as wastewater is sufficient treatment under anaerobic and/or anoxic conditions. Accordingly, in some embodiments the aqueous influent is substantially anoxic. In some embodiments, the aqueous influent is substantially anaerobic.

An excess of algae growth liquid may accumulate in the reservoir in embodiments where influent is added. Accordingly, in some embodiments, the method further comprises removing an amount of liquid from the reservoir to maintain a desired level of algae growth liquid in the reservoir.

As algae grow in the algae growth liquid, the algae growth becomes more viscous and more turbid. Additionally, a high algae density potentially encourages colony behavior and/or sessile forms of algae, and also potentially induces some algae to adopt non-photosynthetic metabolism. Accordingly, in some embodiments, the algal density is maintained at not greater than 25%, not greater than 22% and even not greater than 20% (weight percent of wet algae to wastewater) densities found to yield acceptable results. Accordingly, in some embodiments, the method further comprises harvesting algae from the algae growth liquid, (e.g., by harvesting, for example with a skimmer, or an Archimedean screw). In some embodiments, the harvesting is substantially continuous.

Embodiments of the method according to the teachings herein may be implemented using any suitable device. That said, some embodiments of the methods according to the teachings herein are advantageously implemented using a device according to the teachings herein.

Device for Growing Algae

According to an aspect of some embodiments of the teachings herein, there is provided a device for growing algae, comprising:

a. a reservoir suitable for holding algae growth liquid; and b. a liquid transport assembly defining a conduit for algae growth liquid from the reservoir to a first position of the liquid transport assembly, the first position higher than the reservoir, wherein the first position includes at least one aperture, the at least one aperture configured to allow algae growth liquid removed from the reservoir to move back to the reservoir while passing through a gaseous atmosphere.

In some embodiments, the reservoir is located directly below the first position. In some embodiments, such a configuration allows the device to have a relatively small "footprint", that is to say, require a relatively small area.

In some embodiments, the device (inter alia, by suitable configuration of the liquid transport assembly and the first position) is configured to drop algae growth liquid from the first position of the liquid transport assembly towards the reservoir, thereby effecting the moving back to the reservoir through the gaseous atmosphere.

In some embodiments, the device further comprises a liquid transport device configured to force algae growth liquid from the reservoir through the liquid transport assembly to the first position. In some embodiments, the liquid transport device is a pump, for example, a circulation pump, an Archimedes' screw or a screw conveyer.

In some embodiments, the device is configured so that during at least part of the movement of algae growth liquid from the first position of the liquid transport assembly towards the reservoir, the algae growth liquid is in contact substantially exclusively with the gaseous atmosphere.

In some embodiments, at least one aperture of the liquid transport assembly is configured so that algae growth liquid moving back to the reservoir adopts a high surface area form, for example as described above. For instance, in some embodiments, at least one aperture is a gap, slit or opening configured to produce a sheet of algae growth liquid. Additionally or alternatively, in some embodiments at least one aperture is a plurality of holes or perforations configured to produce a plurality of droplets or streams of algae growth liquid. Typically, such apertures are relatively large, in some embodiments the apertures being at least 16 square millimeter in area. In some embodiments, the first position comprises at least one apertured tube, so that the algae growth liquid moves from the first position as a plurality of drops or streams. In some embodiments, the first composition comprises at least one open-topped conduit (like a trough or gutter), so that the algae growth liquid moves from the first position over the rim of the conduit as a sheet (if the rim is smooth) or as a plurality of individual streams (if the rim has crenelated or similar features).

In some embodiments, the first position is configured to generate a fountain or spray from algae growth liquid. Typically such configuration includes a pressure generator to propel the algae growth liquid.

In some embodiments, the device is configured so that the algae growth liquid cascades from the first position of the liquid transport assembly to the reservoir through a number of intermediate stages. Accordingly, in some embodiments the device further comprises a number of intermediate stages, located at different heights positioned so that algae growth liquid moving from the first position to the reservoir serially contacts a number of intermediate stage, thereby delaying the moving of the algae growth liquid, wherein the number of intermediate stages is at least one. In some embodiments, the intermediate stages are located at different heights one from the other, the heights lower than the first position and higher than the reservoir. In some embodiments the number of intermediate stages is at least two. In some embodiments the number of intermediate stages is at least three. In some embodiments the number of intermediate stages is at least four. In some embodiments the number of intermediate stages is at least five.

In some embodiments, the reservoir is located below the intermediate stage or stages, in some embodiments directly below the intermediate stage or stages. In some embodiments, such configuration allows the device to have a relatively small "footprint", that is to say, occupies a relatively small area.

In some embodiments, at least one of the number of intermediate stages is configured so that algae growth liquid contacting the intermediate stage runs off a rim of the intermediate stage to continue moving to the reservoir (if relevant, first contacting at least one more intermediate stage). For example, in some such embodiments an intermediate stage is a plate, so that algae growth liquid that drops onto the surface of the plate runs off the rim of the plate.

In some embodiments, at least one of the number of the intermediate stages includes at least one aperture (including, for example holes, gaps and slits), the intermediate stage configured so that algae growth liquid contacting the intermediate stage passes through the at least one aperture to continue moving to the reservoir (if relevant, first contacting at least one more intermediate stage). In some such embodiments, an intermediate stage is selected from the group consisting of nets, meshes, apertured components such as plates or bowls, webs, slats and bars. In some such embodiments, a intermediate stage is concave so that the algae growth liquid is accumulated in the concavity of the intermediate stage, but eventually passes through the apertures.

In some embodiments, the device further comprises an illumination component configured to illuminate algae growth liquid held in the device. In some embodiments, the illumination component is configured to illuminate algae growth liquid in the reservoir and/or to illuminate algae growth liquid moving from the liquid transport assembly to the reservoir and/or to illuminate algae growth liquid in the liquid transport assembly.

In some embodiments, the device further comprises a gas-flow generator configured to actively generate gas flow in the atmosphere. Any suitable gas-flow generator may be used, for example a fan or blower.

In some embodiments, the device further comprises a carbon dioxide source configured to add carbon dioxide to the atmosphere. In some embodiments, a carbon dioxide source is functionally associated with the exhaust of a combustor, such as an internal combustion engine or a fossil fuel combustor.

In some embodiments, the device further comprises an at least partially transparent enclosure defining an internal volume containing the first position of the liquid transport assembly, the enclosure constituting a greenhouse. In some embodiments, the liquid transport assembly is also contained in the internal volume of the enclosure. In some embodiments, at least part of, and in some embodiments substantially all of, the reservoir is also contained in the internal volume of the enclosure. In some embodiments, intermediate stages of a device are contained in the internal volume of the enclosure. Typically, a sufficient portion of the enclosure is substantially transparent so as not to substantially interfere with passage of sunlight necessary for photosynthesis. The enclosure may be fashioned of any suitable material including glass and suitable transparent polymers (e.g., polycarbonate, PMMA). In some embodiments, a preferred material is transparent polyethylene film, preferably flexible, as known in the field of agriculture, as these are cheap, readily available and easy to work. In some such embodiments, the device further comprises a gas-flow generator to actively generate a gas flow into the internal volume to maintain the pressure in the internal volume at a higher than ambient air pressure.

In some embodiments, the device further comprises an influent conduit, allowing the addition (in some embodiments continuous addition, in some embodiments intermittent addition, in some embodiments periodic addition) of liquid into the reservoir of the device. In some embodiments, the influent conduit adds influent directly to the reservoir. In some embodiments, the influent conduit adds influent to the liquid transport assembly, especially to the first position. In some embodiments, the influent conduit adds influent to an intermediate stage.

In some embodiments, the device further comprises a drain allowing excess liquid to be removed from the device without overflow, especially when there is influent inflow. In some embodiments, liquid outflow through the drain is regulated to maintain a desired level of algae growth liquid in the reservoir. Any suitable regulating mechanism may be used, for instance a drain hole placed at an appropriate height in the reservoir or a ballcock functionally associated with a mechanism to open a drain or activate a drain pump when the liquid height in the reservoir exceeds a desired height.

In some embodiments, the device further comprises a harvester configured to harvest algae from algae growth liquid held in the device. In some embodiments, the harvester is configured to harvest algae from the liquid transport assembly. In some embodiments, the harvester is configured to harvest algae from the reservoir. Any suitable harvester may be used to harvest algae in a device according to the teachings herein. In some embodiments, the harvester is configured to help clean the reservoir from sessile algae. In some embodiments, the harvester is configured to help stir algae growth liquid held in the reservoir.

Figure 1A:
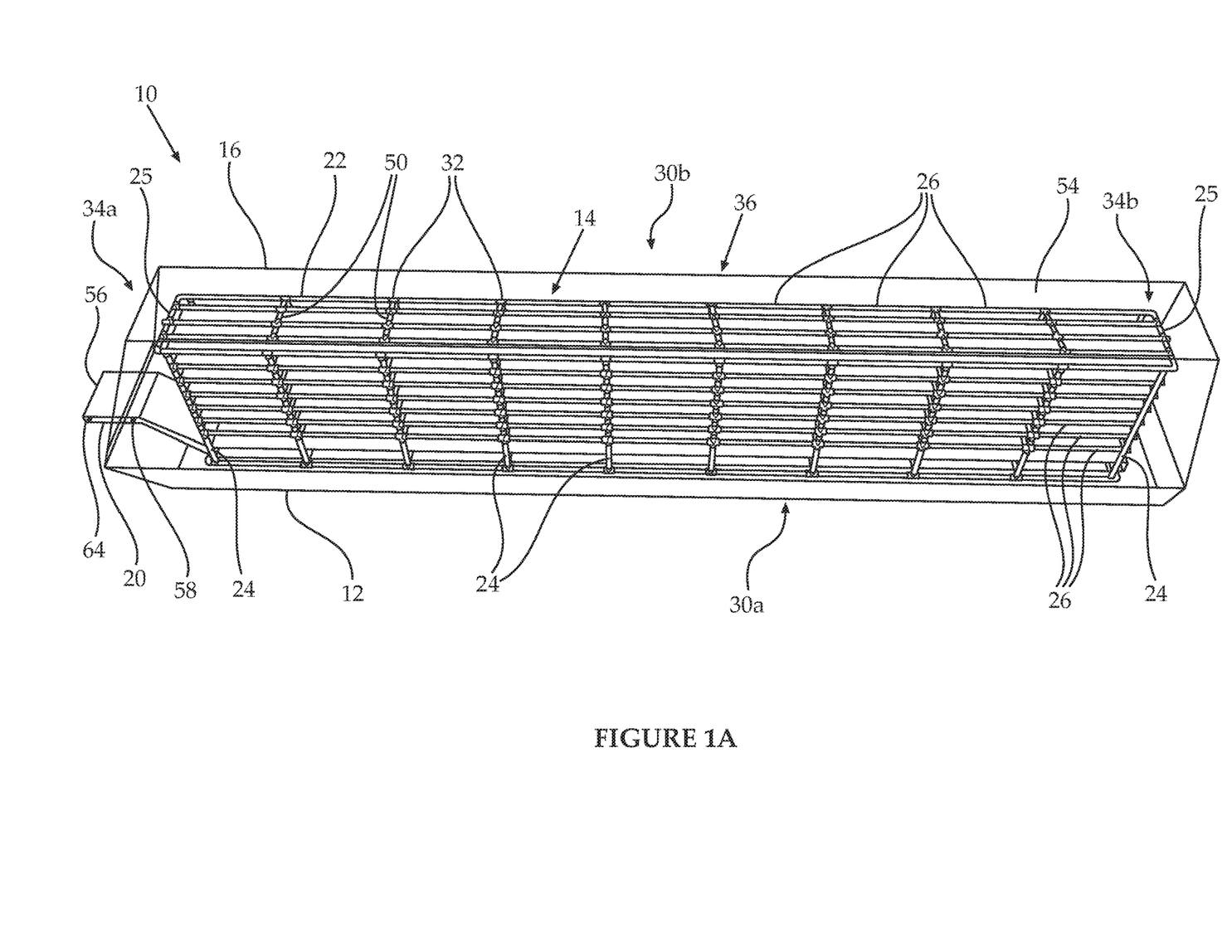
FIG. 1A depicts an embodiment of a device for growing algae as described herein, in perspective.
Figure 1B:
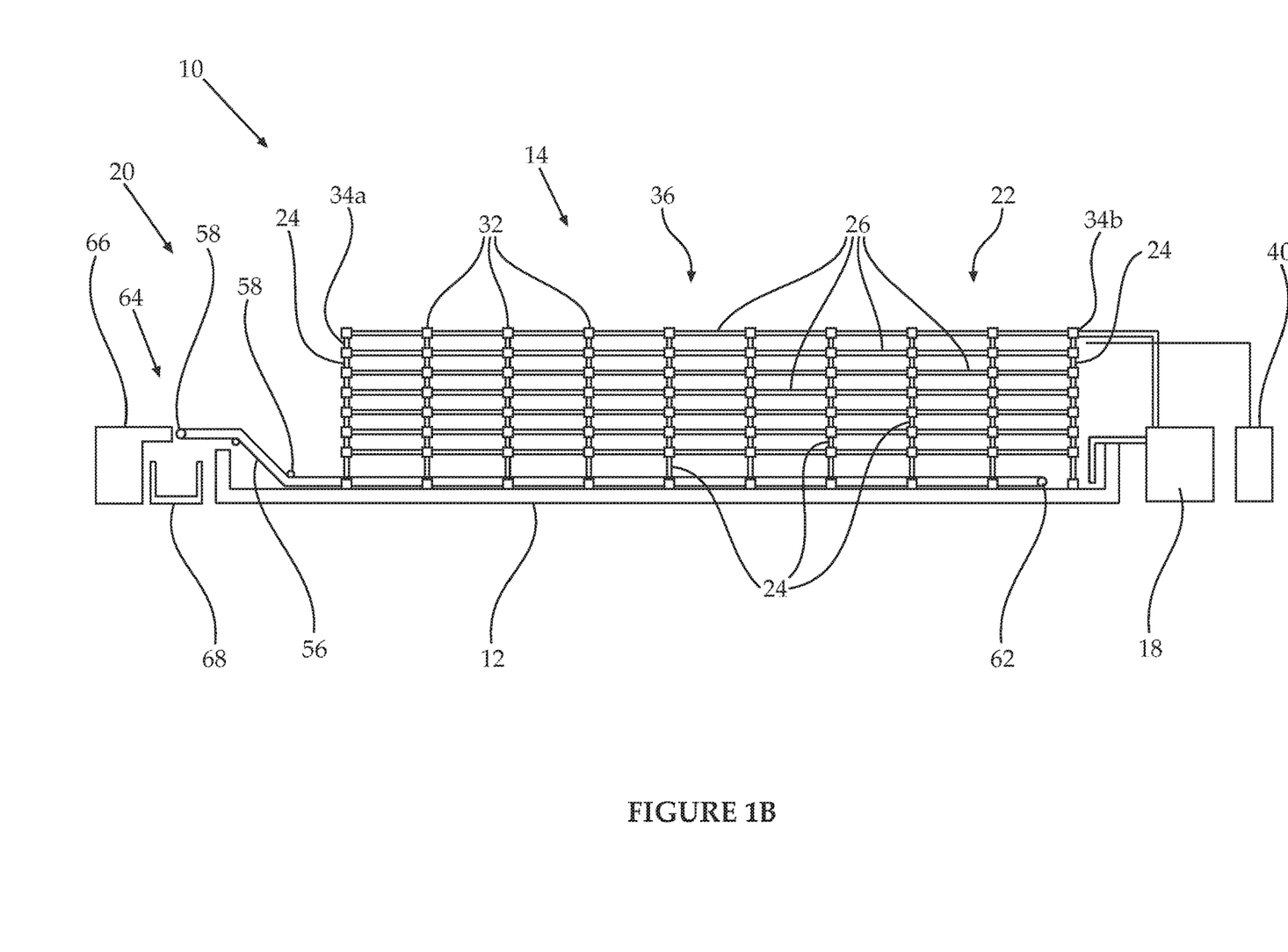
FIG. 1B depicts the device of FIG. 1A, in partial cross section from the side.
Figure 1C:
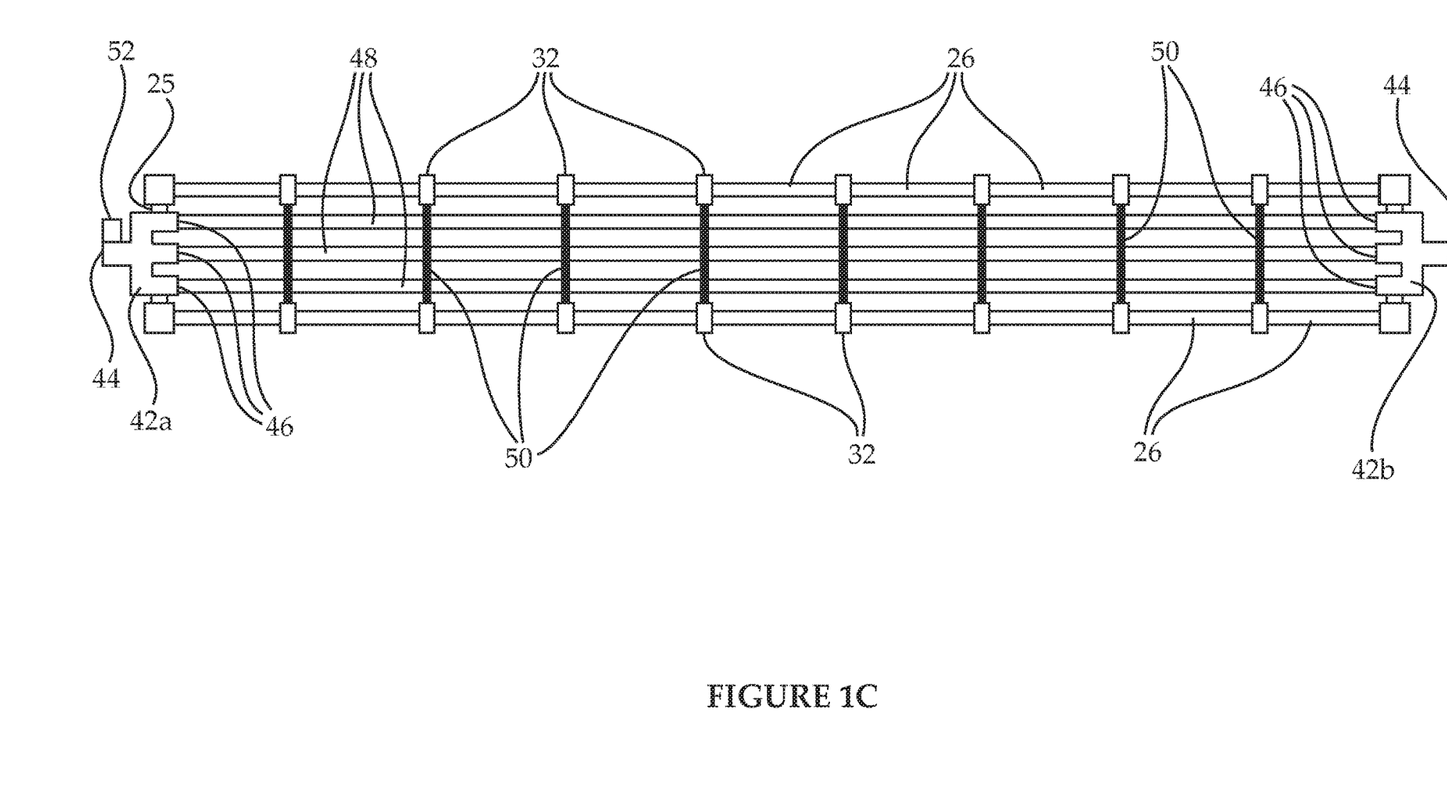
FIG. 1C depicts a liquid transport assembly of the device of FIG. 1A, from the top.
Figure 2A:
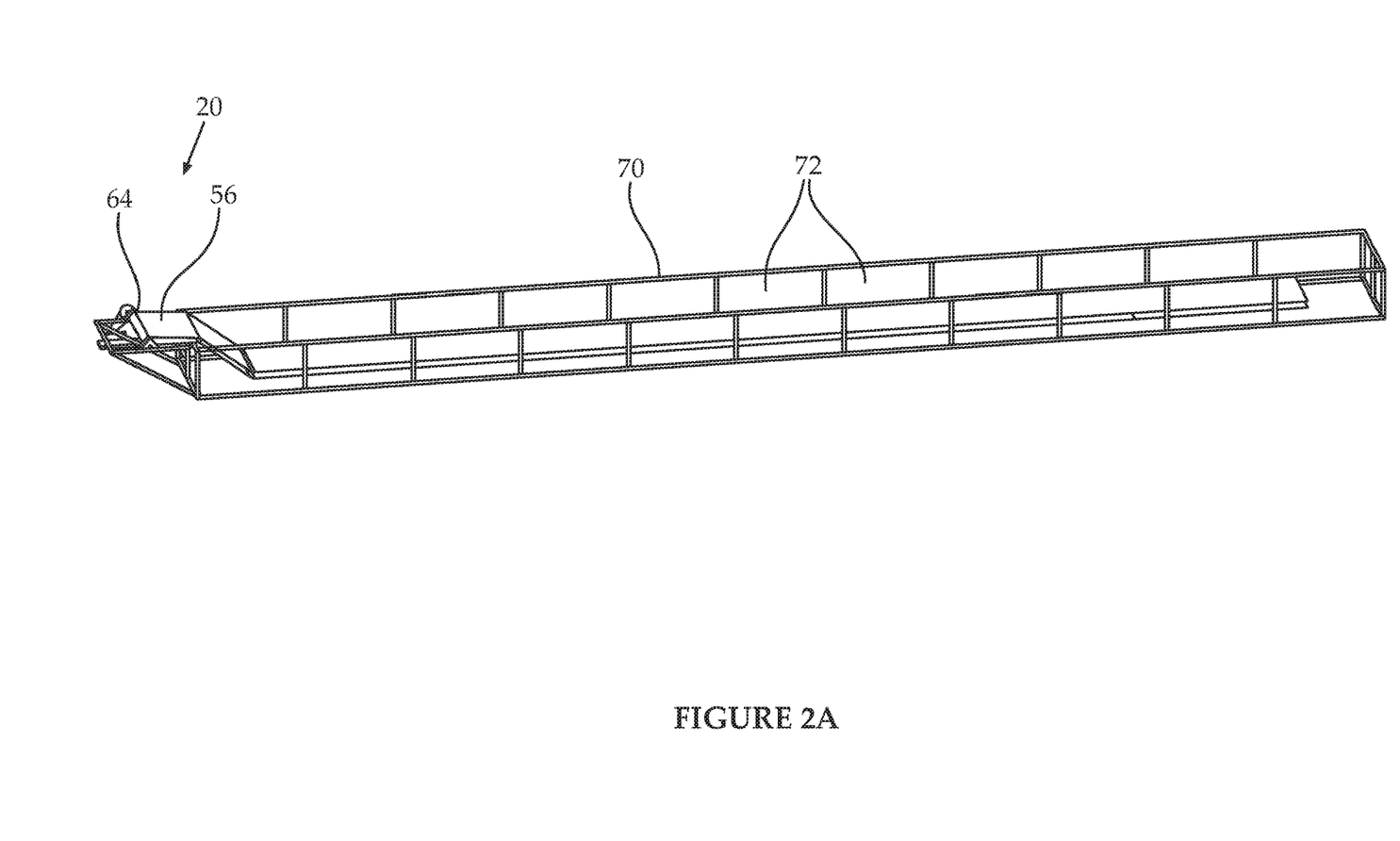
FIGS. 2A and 2B depict an algae harvesting assembly of an embodiment of a device suitable for growing algae as described herein.
Figure 2B:
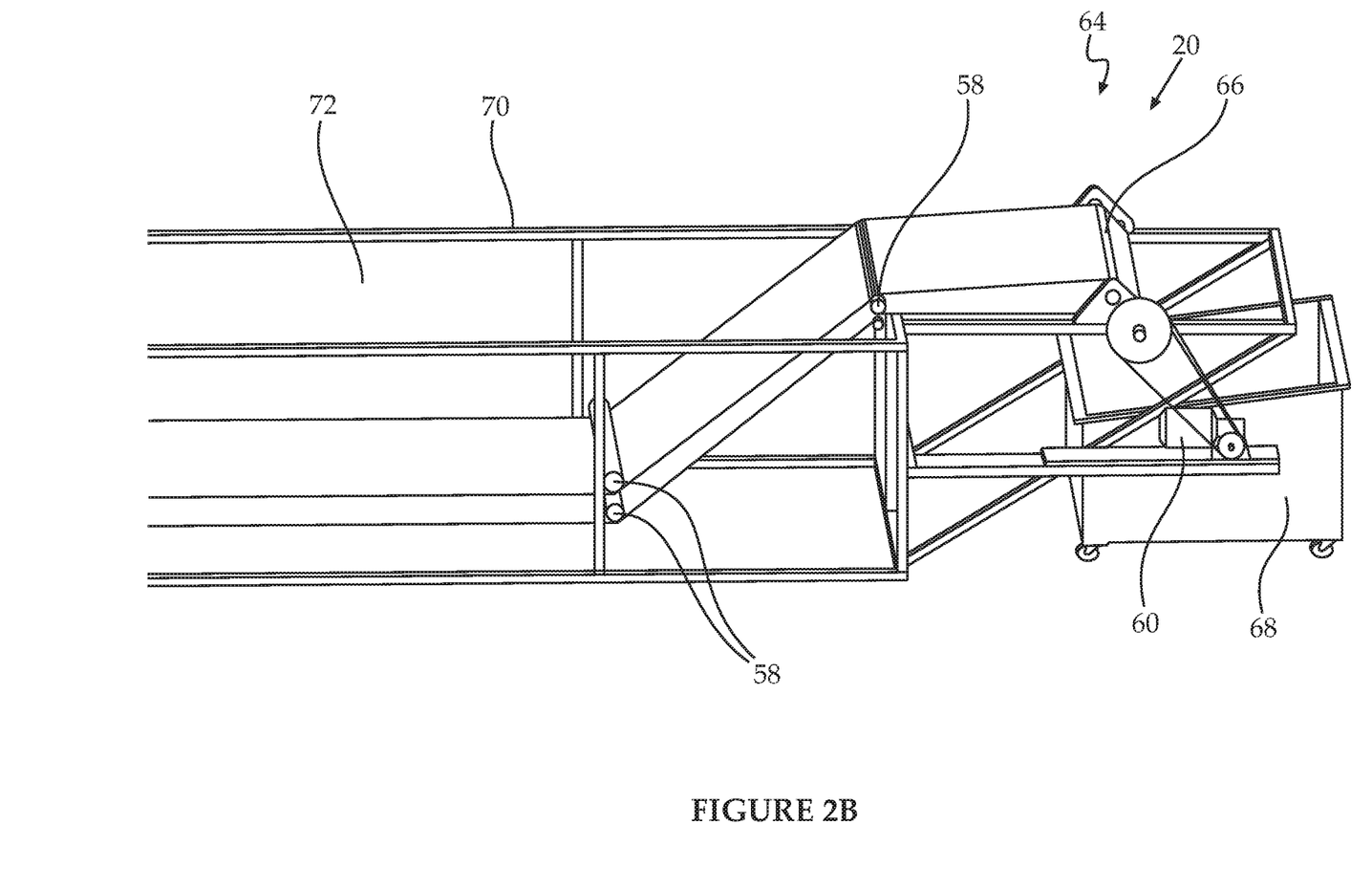
Figure 3:
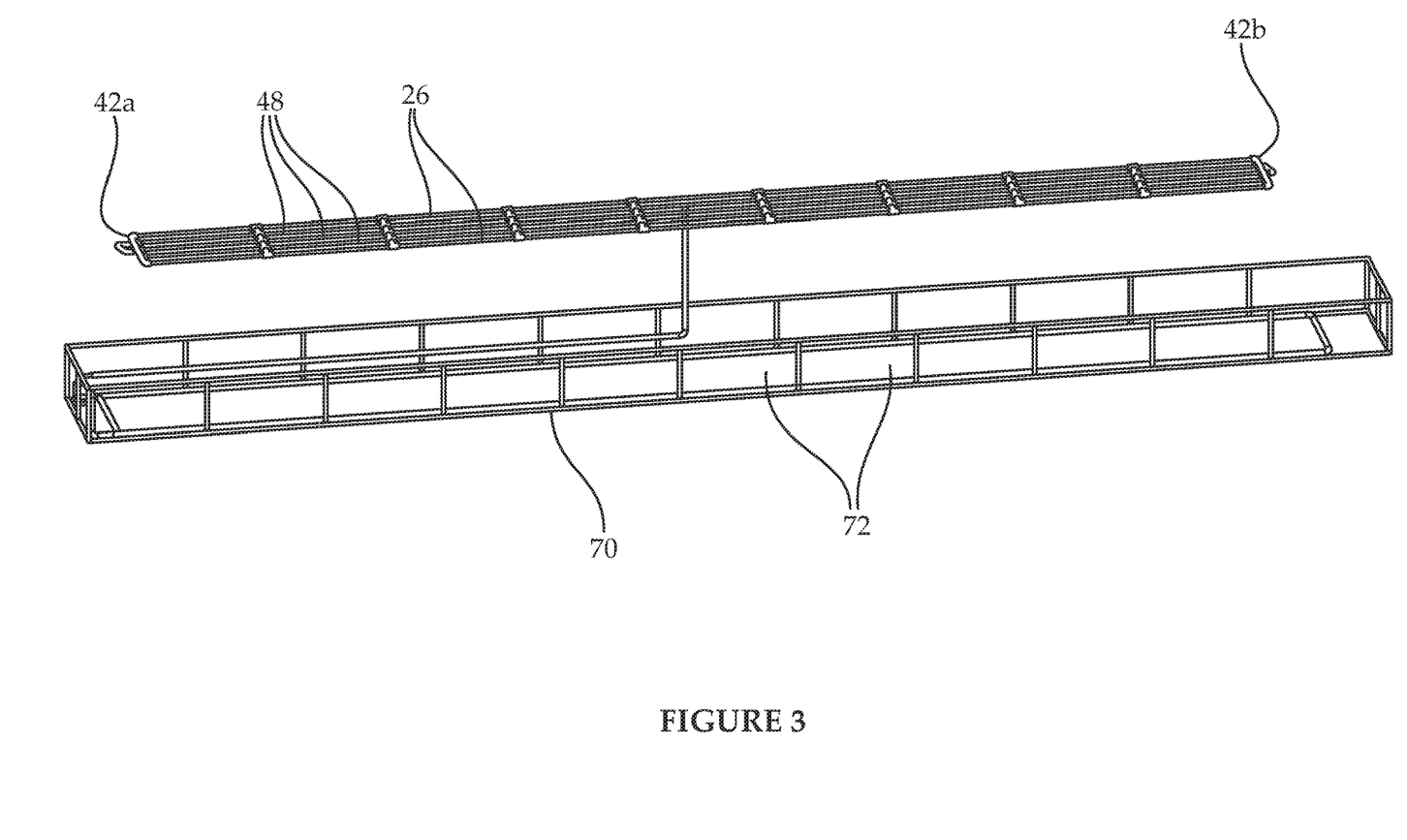
FIG. 3 depicts a liquid transport assembly together with the framework of a reservoir of an embodiment of a device suitable for growing algae as described herein, in perspective.

An embodiment of a device suitable for growing algae in accordance with the teachings herein, device 10, is schematically depicted in FIG. 1. In FIG. 1A, device 10 is schematically depicted in perspective. In FIG. 1B, device 10 is schematically depicted in partial cross section from the side. In FIG. 1C, the liquid transport assembly of device 10 is depicted from the top. In FIGS. 2A and 2B are depicted details of the construction of reservoir 12 and of harvester 20. In FIG. 3, the liquid transport assembly of device 10 is depicted from side perspective.

In FIGS. 1A and 1B, device 10 includes a reservoir 12, a cascade assembly 14, an enclosure 16, a circulation pump 18 and a harvester 20.

Reservoir 12 is a water-tight basin in which the inner void is 11 meters long, 1.2 meters wide and 60 cm deep. Being water-tight, reservoir 12 is configured for holding algae growth liquid. In FIG. 1A, reservoir 12 is seen from the top. In FIG. 1B, reservoir 12 is seen in side cross-section. In FIGS. 2A, 2B and 3, details of the construction of reservoir 12 are seen. Specifically, in FIGS. 2A, 2B and 3, a stainless steel framework 70 defining the size and shape of reservoir is depicted. For use, gaps 72 in framework 70 are filled, for example with rubber panels.

Cascade assembly 14 constitutes the liquid transport assembly and intermediate stages of device 10. Cascade assembly 14 includes a rigid support frame 22 defining a right-angle parallelepiped of vertical tubes 24 and horizontal tubes 26.

A front 30a and back 30b face of support frame 22 are each made of ten 200 cm long 2.5 cm diameter vertical tubes 24, each pair of adjacent vertical tubes 24 mutually connected by seven evenly-spaced 100 cm long 2.5 cm diameter horizontal tubes 26 through right-angle connectors 32.

Each one of ends 34a and 34b of support frame 22 is defined by two terminal vertical tubes 24. The pair of vertical tubes 24 making up end 34a and the pair of vertical tubes 24 making up end 34b are mutually connected by seven evenly-spaced 100 cm long 2.5 cm diameter horizontal tubes 25 through right-angle connectors 32.

Top 36 of support frame 22 is defined by the uppermost nine horizontal tubes 26 of each of faces 30a and 30b, and the uppermost horizontal tubes 25 of ends 34a and 34b.

The bottom (not depicted) of support frame 22 is defined by the bottom ends of the twenty vertical tubes 24 resting on the bottom surface of reservoir 12.

Between any two vertical tubes 24 of back face 30b of support frame 22 are positioned two ~86 cm long linear 21 W fluorescent lamps (Philips Master TL5HE 21 W/830) with a plate reflector configured for directing the lamp light in a 180° arc towards front face 30a through the inner portion of cascade assembly 14. For clarity, in the Figures, none of the eighteen lamps are shown. Lamps are operated by and receive power through a lamp power supply/controller 40. Lamps together with controller 40 constitute an illumination component of device 10.

Each group of twenty horizontal tubes 26 at the same height from the bottom of support frame 22 supports a 90 cm wide 980 cm long net (not seen in FIG. 1) having holes of approximately 9 mm×9 mm defined by 5 mm wide strips (running parallel and perpendicular to faces 30) of 2 mm thick polypropylene. Each net is secured to and stretched between the respective horizontal tubes 26 with the help of cable ties. Each such net constitutes an intermediate stage positioned so that algae growth liquid moving from the liquid transport assembly to reservoir contacts 12 such a net, thereby delaying the movement of the algae growth liquid to reservoir. In device 10 there are six such nets, and therefore six intermediate stages.

Encircled by and coplanar with horizontal tubes 26 of top 36 of support frame 22 is liquid transport assembly of cascade assembly 14, depicted from the top in detail in FIG. 1C and from the side in detail in FIG. 3. At each end 34 of support frame 22 is a manifold 42a and 42b, having a manifold inlet 44 in fluid communication with three manifold outlets 46 in fluid communication with one of three fluid transport tubes 48 (15 mm diameters tubes of PVC) supported along the length thereof by brackets 50, each bracket 50 secured to the top ends of a vertical tube 24 of front face 30a and back face 30b.

On the downwardly facing side of fluid transport tubes 48 are holes, spaced apart by 20 cm. The size of the holes progressively increases from near ends 34 (about 4 mm diameter) towards the middle of fluid transport tubes 48 (about 8 mm diameter). Fluid transport tubes 48 of cascade assembly 14 constitute the first position of the liquid transport assembly of device 10.

Manifold 42a includes a liquid top-up inlet 52.

Circulation pump 18 is a standard water pump that, when activated, pumps liquid from reservoir 12 into inlets 44 of manifolds 42a and 42b, thereby providing algae growth liquid from reservoir 12 to fluid transport tubes 48, the first position of the liquid transport assembly of device 10, by transporting the algae growth liquid from reservoir 12 to the first position.

Enclosure 16 is a closed tent of transparent polyethylene known in the art of agricultural greenhouse that covers cascade assembly 14 and the top of reservoir 12, defining internal volume 54.

Harvester 20 (details in FIGS. 1B, 2A and 2B) is substantially a conveyer belt 56 of woven geotextile driven around spindles 58 by an electrical motor 60. A proximal end 62 of belt 56 is inside reservoir 12 under cascade assembly 14 and between the bottom ends of vertical tubes 24. Belt 56 emerges from reservoir 12 towards a distal end 64 of belt 56. Distal end 64 passes along scraper 66.

For use, device 10 is placed in a location with sufficient sunlight, front face 30 preferably facing southwards so that lamps do not cast shadows into internal volume 54. Reservoir 12 is charged with 6-6.3 m$^3$ of algae growth liquid (substantially water and nutrients (for example, $NH_3$, nitrites, nitrates and/or phosphates) so that the level of algae growth liquid in reservoir 12 is about 50 cm. The algae growth liquid is seeded with spores and/or algae of the species or mixture of species that is desired to grow. Circulation pump 18 is activated to circulate 50 l/min so that 6 m$^3$ of algae growth liquid is cycled in 2 hours. Harvester 20 is activated.

Circulation pump 18 pumps algae growth liquid from reservoir 12 and into cascade assembly 14 through manifold inlets 44, thereby providing algae growth liquid to a first position of the liquid transport assembly of device 10, fluid transport tubes 48. The algae growth liquid enters fluid transport tubes 48 and drips through the holes therein through the atmosphere in contact substantially exclusively with the gaseous atmosphere and devoid of contact with any physical component. The algae growth liquid drops to the first net, and subsequently to each following net back to reservoir 12, in a cascade. The cascading causes the algae growth liquid to have a large surface area in contact with the gas in internal volume 54, and to be vigorously mixed, thereby removing excess oxygen from the algae growth liquid. The cascading absorbs additional $CO_2$ into the algae growth liquid. The cascading ensures that the algae growth liquid is exposed to sufficient sunlight.

Belt 56 of harvester 20 passes through the algae growth liquid in reservoir 12. Algae are caught in the volume of the geotextile. When belt 56 emerges from the algae growth liquid, excess liquid drains from the geotextile leaving algae trapped in belt 56. As belt 56 passes scraper 66 at distal end 64, the thus-harvested algae are scraped off belt 56 into hopper 68 for subsequent recovery and processing.

The motion of belt 56, the action of circulation pump 18 and the cascading of the algae growth liquid ensure that the algae growth liquid in reservoir 12 is sufficiently mixed.

Analogously to the discussed in PCT/IB2012/000884, when there is insufficient light for substantial photosynthesis (e.g., at night), lamps are activated to illuminate the algae growth liquid. Circulation pump 18 and harvester 20 remain activated to continue circulation and harvesting of algae in the algae growth liquid.

Conditions

The amount and nature of nutrients, the rate of circulation, the rate of harvesting and other operating parameters are typically determined by the type of algae that is to be grown and other conditions such as the amount and intensity of sunlight.

In some embodiments, the device is operated under conditions favorable for algal photosynthesis. In some preferred embodiments, the conditions are such that encourage photosynthesis at the expense of other forms of metabolism and/or that encourage algal lipid production and/or discourage lignin production and/or discourage algal settling. Specifically, it is preferable that the algae population be predominantly or entirely microalgae, such as planktonic algae, as opposed to sessile growth algae, as close as possible to unicellular with as little as possible incidence of colony formation. Although not wishing to be held to any one theory, it is believed that in such a state one or more of: the algae growth liquid remains relatively clear with little light scattering so that more light is used for photosynthesis; the cell walls remain relatively thin so light more effectively penetrates into the cell for photosynthesis; the cells have a higher lipid content relative to cellulose content; the cells have a relatively low lignin content relative to cellulose content; the algae growth liquid is more fluid and less viscous; and there is a reduced chance of clogging of the device. At the same time, it is preferred that the algae grow in conditions that discourage swimming behavior and development of swimming organs that expend lipids that are otherwise harvested. Such conditions are described herein, as well as in detail in PCT Patent Application IB2012/000884.

Algae

Any suitable algae or combination of algae may be grown according to the teachings herein. In some embodiments, the algae are mixotrophic and/or photoautotrophic. Although in some embodiments, the algae are of a single species, in some preferred embodiments the algae are of multiple (at least two different) species.

Replenishment of Nutrients and Liquids

Algae growth uses nutrients found in the algae growth liquid. If the nutrients are not replenished, algae growth becomes less optimal. Typically, during use of device 10, the amount of nutrients is replenished, for example by addition into reservoir 12 or through top-up inlet 52. In some embodiments, the level of one or more nutrients is monitored (continuously, intermittently and/or periodically) and replenished with reference to the results of the monitoring.

Photosynthesis and algae harvesting lead to the loss of water and thus, the volume of algae growth liquid. If the water is not replenished, the level of algae growth liquid in reservoir 12 drops and algae growth becomes less optimal. Typically, during use of device 10, the amount of water is replenished, for example by addition into reservoir 12 or through top-up inlet 52. In some embodiments, the level of water is monitored (continuously, intermittently and/or periodically, for example with a float valve) and replenished with reference to the results of the monitoring.

In some embodiments, nutrients are replenished together with water.

Activation of Lamps

As discussed in PCT/IB2012/000884, in some embodiments, algae growth is improved by continuously exposing the algae to light, even if such light is insufficient for substantial photosynthesis.

In some embodiments, lamps are activated when there is insufficient sunlight to support substantial photosynethesis (e.g., night time), for example with the help of a light detector or a timer functionally associated with lamp controller 40. In some embodiments, lamps are continuously activated.

In some embodiments, lamp controller 40 is configured to generate electricity, e.g., from sunlight, and/or store electricity for powering lamps. For example, in some embodiments, lamp controller 40 includes photovoltaic cells and rechargeable batteries. When there is sufficient sunlight to support photosynthesis, the photovoltaic cells generate electricity that is stored in the batteries. When there is insufficient sunlight to support photosynthesis, lamp controller 40 draws electricity from the batteries to power lamps.

In some embodiments, in order to avoid or help prevent algae in the algae growth liquid held in the device from adopting non-photosynthetic metabolism (e.g., respiratory metabolism) when there is insufficient sunlight to support sufficient photosynthesis (that is to say, the intensity of sunlight is low so that a non-negligible portion of the algae tends to adopt non-photosynthetic metabolism), the algae growth water in the device is illuminated with artificial light. The intensity of the artificial light is sufficient to help avoid algae adopting non-photosynthetic metabolism.

In device 10, the position of lamps is such that illumination component is configured to primarily illuminate algae growth liquid passing through cascade assembly 14, that is to say, algae growth liquid passing from the liquid transport assembly to the reservoir. In some embodiments of the device 10, an illumination component is configured additionally or alternatively to primarily illuminate algae growth liquid in the reservoir (e.g., by submerged or properly oriented lamps), and additionally or alternatively, to primarily illuminate algae growth liquid in the liquid transport assembly (e.g., fluid transfer tubes 48).

Activation of Circulation Pump 18

As discussed in PCT/IB2012/000884, in some embodiments algae growth is improved by the moving the algae at different rates during a period of time. In some embodiments, such movement prevents the algae settling and/or forming colonies that, inter alia, may clog the device or make (synthesize) excessive cellulose. At the same time, in some such embodiments, the movement of algae at different rates discourages the development of swimming organs and consequent swimming behavior that expends (metabolizes) lipids that could otherwise be harvested.

Typically, circulation pump 18 is continuously activated to continuously pump algae growth liquid from reservoir 12 into manifolds 42a and 42b. Algae that are pumped by circulation pump 18, or drop in the cascade assembly 14 move at a relatively fast rate. Most algae in reservoir 12, or algae that rest on the nets of cascade assembly 14 move at a relatively slow rate.

In some embodiments, a circulation pump is activated non-continuously, for example, intermittently or periodically, especially when there is insufficient light to support substantial photosynthesis. In some embodiments, the rate at which a circulation pump circulates algae growth liquid is reduced at certain times, for example when there is insufficient light to support substantial photosynthesis.

In some embodiments, in order to avoid the algae settling in the device, in some embodiments when there is insufficient sunlight to support sufficient photosynthesis, the algae growth water in the device is circulated, substantially as described herein, that is to say discontinuously or continuously, at a rate sufficient to help avoid algae settling in the device.

Harvester

As depicted in the figures, especially FIGS. 1B, 2A and 2B, in device 10, belt 56 is suspended over the bottom of reservoir 12. When electrical motor 60 is activated, belt 56 is moved around spindles 58. In some embodiments, such a belt or equivalent component contacts the bottom of a reservoir, thereby scraping the bottom of the reservoir when activated to help clean the reservoir from sessile algae.

In device 10, harvester 20 is an integrated component configured to harvest algal biomass. Harvester 20 (by being deployed along the length and near the bottom of reservoir 12) is also configured for stirring the algae growth liquid in reservoir 12, in some embodiments assisting in preventing clogging and/or settling of algae and/or undesirable modes of algal growth.

In some embodiments, a drain through which liquid is removed from the device is located at the bottom of the reservoir. A filter is positioned over the drain inlet to prevent substantial passage of algae through the drain. In some such embodiments, the belt of a harvester such as described above scrapes away accumulated algae from the filter surface, preventing clogging thereof.

In device 10, harvester 20 is substantially a conveyer belt. In some embodiments, other suitable harvesters are used, for example, harvesters based on Archimedes' screws and the like. The algal biomass may be harvested using any suitable method or device, preferably continuously, and preferably at a rate that is dependent on the rate of algal growth to maintain the algae population in the algae growth liquid at a desired density. Specifically, different species of algae respond differently to population density. There is typically a range of population densities that provide preferred growing conditions. By varying the rate of harvesting, e.g., in device 10 by varying the rate of movement of the conveyer belt, the population density of algae in the algae growth liquid can be regulated.

Cascade Assembly

In device 10, fluid transport tubes 48 of cascade assembly 14 constitute the first position of the liquid transport assembly of device 10 to which algae growth liquid is transported by circulation pump 18 from reservoir 12, and from which the algae growth liquid is subsequently dropped to move past the intermediate stages back to reservoir 12. The algae growth liquid exits fluid transport tubes 48 through holes on the downwardly facing side thereof. Depending on the pressure of algae growth liquid in fluid transport tubes 48, the algae growth liquid exits as a plurality of discrete drops or streams.

In some embodiments, a first position of a device has another configuration. For instance, in some embodiments of a device, the first position includes a slit tube or an open-topped conduit (like a gutter or trough) and the algae growth liquid exits through the slit or over the rim as a sheet (if the rim/slit is smooth) or as a plurality of discrete drops or streams (if the rim has features such as teeth or crenellations), Cascade assembly 14 of device 10 includes six intermediate stages. Algae growth liquid moving from the liquid transport assembly to reservoir 12 serially contacts each one of the six intermediate stages, in a cascade. In some embodiments of a device according to the teachings herein there are more than six intermediate stages. In some embodiments of a device according to the teachings herein there are fewer than six intermediate stages, for example one, two, three, four or five intermediate stages. In some embodiments of the device, there are no intermediate stages. That said, when there is no intermediate stage or even one or two intermediate stage, the time that a portion of algae growth liquid spends moving quickly, is susceptible to gas exchange and is exposed to sufficient sunlight, is limited which may provide inferior results.

In device 10, algae growth liquid passes through apertures in the intermediate stages, the holes in the nets. An advantage of nets is that these adopt a somewhat concave shape able to hold algae growth liquid for a certain period of time before the liquid drains through the holes. In some embodiments, one or more intermediate stages is not concave but includes apertures (e.g., perforated plates/bowls of metal or plastic, rigid arrangements of bars or slits), so that liquid that does not pass through the apertures runs off the edges of the intermediate stage. In some embodiments, one or more intermediate stages is devoid of apertures (e.g., solid plates of metal or plastic), so that liquid contacting the intermediate stage runs off the edges of the intermediate stage.

Reservoir

In device 10, reservoir 12 is an open basin. In some embodiments, other suitable reservoir are used, for example, a substantially closed reservoir.

In device 10, reservoir 12 is located directly below the various components of the liquid transport assembly and the intermediates stages, such as cascade assembly 14, allowing device 10 to have a small footprint.

In some embodiments, a reservoir is not located directly below the liquid transport assembly and the intermediate stages. For example, in some embodiments, the liquid transport assembly and intermediate stages are located in a first location (for example, suspended from or attached to a structure like a wall or roof) and are functionally associated through liquid conduits with the reservoir (for instance, a barrel or pool) that is located in a second location able to bear the weight of the reservoir and/or that is more convenient and/or more esthetic.

Enclosure

In device 10, enclosure 16 substantially encloses the other components of the device, but is not sealed, in the manner of a greenhouse. In some embodiments, an enclosure is sealed, substantially preventing any uncontrolled entry of materials, such as gases, into the device.

In some embodiments, in order to maximize the conversion of carbon dioxide and nutrients to algal biomass allowing maximal production of desired products such as lipids, it is preferred that the algae grow in the device without competition from other microorganisms. Accordingly, in some embodiments the device is closed, and in some embodiments sealed to prevent microorganisms from the surroundings from entering the internal volume of the device.

Carbon Dioxide and Gases

In device 10, ambient air enters internal volume 54 because enclosure 16 is not sealed, the ambient air providing the carbon dioxide required by algae for photosynthesis. Air flow inside the internal volume of enclosure 16 occurs due to entry of the ambient air and the turbulence caused by the algae growth liquid dropping through cascade assembly 14 to reservoir 12.

In some embodiments, ambient air or other gas is actively introduced into internal volume 54 of enclosure 16, using a gas-flow generator such as a fan, pump or blower. Such a gas-flow generator actively generates gas flow in the atmosphere inside enclosure 16. In some such embodiments, the air is filtered. In some such embodiments, the air is treated, for example by filtration or ultraviolet irradiation, to prevent the entry of undesirable microorganisms and/or algal spores.

Carbon dioxide is a greenhouse gas that is typically released into the atmosphere, in some instances at a cost. It is preferable, both for environmental and economic reasons to sequester rather than release carbon dioxide. Further, a lack of carbon dioxide in the algae growth liquid may potentially induce some algae to adopt non-photosynthetic metabolism (e.g., respiratory metabolism) while sufficient $CO_2$ in the algae growth liquid may support photosynthetic metabolism of the algae.

In some embodiments, a gas including a higher than ambient air amount of carbon dioxide (0.04%) is introduced (in some embodiments, actively introduced) into the internal volume of the enclosure so that the atmosphere therein has a carbon dioxide content higher than ambient air (0.04%). In some embodiments, a relatively high carbon dioxide content in the atmosphere above the algae growth liquid promotes growth better than does direct introduction of carbon dioxide (e.g., bubbling) into the algae growth liquid.

Accordingly, in some embodiments, carbon dioxide gas is added to internal volume 56 of the device. In some embodiments, the carbon dioxide is from a carbon dioxide source such as the exhaust of an internal combustion engine or effluent of an industrial process, typically in proximity to where the teachings herein are implemented. In some embodiments, carbon dioxide is isolated (e.g., by distillation) from some source for example, from the exhaust of an internal combustion engine or industrial process, typically in proximity to where the teachings herein are implemented and the relatively-pure carbon dioxide added into the internal volume of the device.

In some embodiments, the device is operated at above ambient pressure, typically 0.2% to 5%, 0.5% to 5%, and even 1% to 5%, above ambient pressure, typical by operating a gas-flow generator such as a blower, pump or fan that continuously introduces a gas such as air or carbon dioxide$_2$-enriched air. Such pressure helps prevent contamination of the internal volume of the device.

In some embodiments, the device includes a vent allowing escape of gases from the internal volume. In some embodiments, the device includes a one-way valve (e.g., check valve) that allows escape of gases from internal volume 56 but prevents contaminants from the surroundings from entering internal volume 56.

Drain

In some embodiments, a device includes a passive drain positioned at a desired level in reservoir 12. If the level of liquid in reservoir 12 reaches the drain, the liquid is drained off rather than overflows from reservoir 12. In some embodiments, the drain is an active drain, that is to say, has a mechanism that detects a level of liquid in the reservoir, and when the level exceeds a threshold, opens a drain to allow liquid to drain from the reservoir. As noted above, one suitable such mechanism includes a ballcock as known in the art.

In some embodiments, the drain is provided with a filter to reduce the amount or prevent the release of algae through the drain. In some embodiments, the drain is functionally associated with a mechanism to kill algae spores, for example, a heater or UV lamp.

Dimensions

Some embodiments of device as described herein are scaleable, that is to say, can be easily built larger or smaller according to the same basic plan without undue effort depending on a desired capacity. Some embodiments can be easily changed in size. Some embodiments are modular. Some embodiments are made with using commonly available materials and can be assembled and operated by non-expert labor.

Harvested Algal Biomass

In some embodiments, the harvested algal biomass is used, for example, as animal feed (livestock, aquaculture) or fertilizer.

In some embodiments, the harvested algal biomass is and separated to lipids (e.g., for use as biodiesel) and solids, such as cellulose (e.g., for fuel, digestion or fermentation to bioethanol). In embodiments, growth conditions are selected for encouraging photosynthetic metabolism and planktonic modes while discouraging non-photosynthetic metabolism, settling, sessile modes and development of colonies and swimming behaviors, as noted above, in some embodiments the lipid content in the algal biomass is unusually high and the lignin content is relatively low.

Separation of the algal biomass into a lipid stream and a solid (cellulose and lignin) stream can be performed in any suitable fashion, for example as known in the art. For example, in some embodiments, the algal biomass is sonicated to rupture cell walls and centrifuged with a carrier (dichloroethane, dichloromethane, acetone, freon) to separate the streams. In some embodiments, such separation is relatively easy due to the relatively thin cell walls of the algal biomass. As a result of the centrifugation, the algal biomass is separated into a lipid layer, a solid material layer, a water layer and a mineral layer (typically including $SiO_2$ from diatomic algae and/or $CaCO_3$ from green algae).

As known in the art, the lipid stream may be used, for example, for manufacture of biodiesel. In some embodiments, isolation of the lipid stream and use thereof as fuel is done locally, to generate power to implement the teachings herein.

As known in the art, the solid stream may be used, for example, as animal feed, or as a fertilizer, may be burnt (as a fuel or for disposal), or more typically may be fermented for the manufacture of bioethanol. In some embodiments, the dearth of lignin in the solid stream makes fermentation exceptionally advantageous.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A device for growing algae comprising:
   a reservoir, suitable for holding algae growth liquid;
   a rigid support frame composed from a plurality of horizontal and vertical framing members and having a horizontal cross-section defining a foot print of the rigid support frame, a bottom of the rigid support frame being located within the reservoir, a top of the rigid frame defined by a plurality of uppermost of the horizontal members of the rigid support frame; and
   a liquid transport assembly defining a conduit for algae growth liquid from said reservoir to a first position of said liquid transport assembly, said first position higher than said reservoir, the liquid transport assembly includes a fluid transport conduit, the fluid transport conduit having a first end located at one side of the top of the rigid support frame, extending towards at an opposite side of the top of the rigid support frame and having a second end located at the opposite side of the top of the rigid support frame,
   wherein the fluid transport conduit is located along the top of the rigid support frame
   wherein the fluid transport conduit is located along the top of the rigid support frame defining said first position and includes at least one aperture, said at least one aperture configured to allow algae growth liquid removed from said reservoir to move back to said reservoir while passing through a gaseous atmosphere;
   wherein said first position is contained in an internal volume of an at least partially transparent enclosure so that said enclosure constitutes a greenhouse;
   wherein said reservoir is located directly below said first position of said liquid transport assembly,
   wherein the device further comprises:
   at least one intermediate stage located lower than said first position and higher than said reservoir and within the foot print, configured so that during said moving of the algae growth liquid to said reservoir, the algae growth liquid drops from said first position to said reservoir through an intermediate stage, thereby dropping from said first position to said intermediate stage and dropping from said intermediate stage towards said reservoir, and
   wherein during said dropping the algae growth liquid is in contact substantially exclusively with said gaseous atmosphere.

2. The device of claim 1, further comprising a liquid transport device configured to force algae growth liquid from said reservoir through said liquid transport assembly to said first position.

3. The device of claim 1, wherein said at least one aperture is configured so that algae growth liquid moving back to said reservoir adopts a high surface area form.

4. The device of claim 3, wherein the fluid transport conduit is an apertured tube.

5. The device of claim 3, wherein the fluid transport conduit is an open-topped conduit.

6. The device of claim 1, at least one said intermediate stage configured so that algae growth liquid runs off an edge of said intermediate stage to continue moving to said reservoir.

7. The device of claim 1, at least one said intermediate stage including at least one aperture, configured so that algae growth liquid passes through said at least one aperture to continue moving to said reservoir.

8. The device of claim 7, wherein a said intermediate stage is selected from the group consisting of a net, a mesh, a web, an apertured component, slats and bars.

9. The device of claim 1, further comprising a gas-flow generator configured to actively generate gas flow in said atmosphere.

10. The device of claim 1, further comprising a carbon dioxide source configured to add carbon dioxide to said atmosphere.

11. The device of claim 1, said liquid transport assembly contained in said internal volume of said enclosure.

12. The device of claim 1, said reservoir contained in said internal volume of said enclosure.

13. The device of claim 1, further comprising a harvester configured to harvest algae from algae growth liquid held in the device.

14. The device of claim 1, wherein said reservoir is located directly below said at least one intermediate stage.

15. The device of claim 1, wherein said at least one intermediate stages is two or more intermediate stages at different heights one from the other.

16. The device of claim 1, wherein said at least one intermediate stages is three or more intermediate stages.

17. The device of claim 1, wherein said at least one intermediate stages is four or more intermediate stages.

18. The device of claim 1, wherein said at least one intermediate stages is five or more intermediate stages.

* * * * *